(12) United States Patent
Omwancha et al.

(10) Patent No.: US 11,096,890 B2
(45) Date of Patent: Aug. 24, 2021

(54) CHEWABLE DOSAGE FORMS CONTAINING SITAGLIPTIN AND METFORMIN

(71) Applicant: Merck Sharp & Dohme Corp., Rahway, NJ (US)

(72) Inventors: Wycliffe S. Omwancha, East Brunswick, NJ (US); Rubi Burlage, Florham Park, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/141,495

(22) Filed: Sep. 25, 2018

(65) Prior Publication Data

US 2019/0099367 A1  Apr. 4, 2019

Related U.S. Application Data

(60) Provisional application No. 62/565,549, filed on Sep. 29, 2017.

(51) Int. Cl.

| | | |
|---|---|---|
| *A61K 9/00* | (2006.01) | |
| *A61K 31/4985* | (2006.01) | |
| *A61K 31/155* | (2006.01) | |
| *A61K 47/36* | (2006.01) | |
| *A61K 47/10* | (2017.01) | |
| *A61K 47/14* | (2017.01) | |
| *A61K 47/12* | (2006.01) | |
| *A61K 47/26* | (2006.01) | |
| *A61K 47/44* | (2017.01) | |
| *A61K 9/20* | (2006.01) | |

(52) U.S. Cl.
CPC .......... *A61K 9/0056* (2013.01); *A61K 31/155* (2013.01); *A61K 31/4985* (2013.01); *A61K 47/10* (2013.01); *A61K 47/12* (2013.01); *A61K 47/14* (2013.01); *A61K 47/26* (2013.01); *A61K 47/36* (2013.01); *A61K 47/44* (2013.01); *A61K 9/2059* (2013.01)

(58) Field of Classification Search
CPC ...... A61K 9/0056; A61K 47/10; A61K 47/26; A61K 47/12; A61K 47/14; A61K 47/44; A61K 47/36; A61K 31/155; A61K 31/4985; A61K 9/2059
See application file for complete search history.

(56) References Cited

U.S. PATENT DOCUMENTS

| | | | |
|---|---|---|---|
| 6,699,871 B2 | 3/2004 | Edmondson et al. | |
| 7,326,708 B2 | 2/2008 | Cypes et al. | |
| 8,414,921 B2 | 4/2013 | Kamali | |
| 2007/0128251 A1* | 6/2007 | Paulsen | A61K 9/1652 424/439 |
| 2010/0104689 A1* | 4/2010 | Thorengaard | A61K 9/2077 426/5 |
| 2010/0323011 A1 | 12/2010 | Pourkavoos | |
| 2010/0330177 A1* | 12/2010 | Pourkavoos | A61K 9/209 424/465 |
| 2012/0202820 A1* | 8/2012 | Rimkus | A61K 9/2027 514/249 |
| 2015/0086621 A1* | 3/2015 | Gahler | A61K 31/155 424/451 |
| 2015/0374688 A1* | 12/2015 | Jain | A61K 9/209 424/472 |
| 2016/0228379 A1* | 8/2016 | Kumar | A61K 9/0095 |
| 2019/0099368 A1 | 4/2019 | Omwancha | |

FOREIGN PATENT DOCUMENTS

| | | | | |
|---|---|---|---|---|
| WO | WO-2013077825 A1 * | 5/2013 | ........... | A61K 9/2077 |
| WO | 2015160678 A1 | 10/2015 | | |

OTHER PUBLICATIONS

Chewable metformin article published Oct. 12, 2012; retrieved from the web Aug. 25, 2020 (Year: 2012).*
Janumet prescribing information approved 2007; retrieved from the web Aug. 26, 2020 (Year: 2007).*
Campbell, Rationale for Dipeptidyl Peptidase 4 Inhibitors: A New Class of Oral Agents for the Treatment of Type 2 Diabetes Mellitus, Ann. Pharmacother, 2007, 51-60, 41.
Combettes et al., GLP-1 and Type 2 Diabetes: Physiology and New Clinical Advances, Curr. Opin. Pharmacol, 2006, 598-605, 6.
Deacon, Dipeptidyl Peptidase 4 Inhibition with Sitagliptin: A New Therapy for Type 2 Diabetes, Exp. Opin. Invest. Drugs, 2007, 533-545, 16.
Drucker et al., Sitagliptin, Nature Reviews Drug Discovery, 2007, 109-110, 6.
Gallwitz, Sitagliptin with Metformin: Profile of a Combination for the Treatment of Type 2 Diabetes, Drugs of Today, 2007, 681-689, 43(10).
Gallwitz, Sitagliptin: Profile of a Novel DPP-4 Inhibitor for the Treatment of Type 2 Diabetes, Drugs of Today, 2007, 13-25, 43 (1).
Goldstein et al., Effect of Initial Combination Therapy with Sitagliptin, a Dipeptidyl Peptidase-4 Inhibitor, and Metformin on Glycemic Control in Patients with Type 2 Diabetes, Diabetes Care, 2007, 1979-1987, 30.
Green et al., Inhibition of Dipeptidyl Peptidase IV Activity as a Therapy of Type 2 Diabetes, Exp. Opin Emerging Drugs, 2006, 525-539, 11.
Lyseng-Williamson, Sitagliptin, Drugs, 2007, 587-597, 67.
Stonehouse et al., Management of Type 2 Diabetes: The role of Incretin Mimetics, Expert Opinion on Pharmacotherapy, 2006, pp. 2095-2105, 7 (15).

* cited by examiner

*Primary Examiner* — Sarah Pihonak
*Assistant Examiner* — Jason Deck
(74) *Attorney, Agent, or Firm* — Eric A. Meade; John C. Todaro

(57) ABSTRACT

The present invention provides a chewable dosage form having a matrix comprising: a combination of active pharmaceutical ingredients which is metformin hydrochloride and sitagliptin or a pharmaceutically acceptable salt thereof; a fully or partially pregelatinized starch, a polyethylene glycol polymer; a lubricant; an emulsifier; a flavoring agent; and a sweetener. The present invention also provides a method of treating diabetes, e.g., non-insulin dependent (Type 2) diabetes mellitus, comprising administering a therapeutically effective amount of the chewable dosage form to a mammalian patient in need thereof.

9 Claims, 2 Drawing Sheets

CHEWABLE DOSAGE FORMS CONTAINING SITAGLIPTIN AND METFORMIN

CROSS REFERENCE TO RELATED APPLICATIONS

This application is a U.S. non-provisional application which claims the benefit of provisional Application No. 62/565,549, filed Sep. 29, 2017.

FIELD OF THE INVENTION

The present invention relates to pharmaceutical formulations useful for administering a combination of sitagliptin and metformin to a mammalian patient.

BACKGROUND OF THE INVENTION

Identification of any publication in this section or any section of this application is not an admission that such publication is prior art to the present invention.

Type 2 diabetes is a chronic and progressive disease arising from a complex pathophysiology involving the dual endocrine effects of insulin resistance and impaired insulin secretion. The treatment of type 2 diabetes typically begins with diet and exercise, followed by or antidiabetic monotherapy. For many patients, these regimens do not sufficiently control glycemia during long-term treatment, leading to a requirement for combination therapy within several years following diagnosis. However, co-prescription of two or more oral antidiabetic drugs may result in treatment regimens that are complex and difficult for many patients to follow. Combining two or more oral antidiabetic agents into a single tablet provides a potential regimen of delivering combination therapy without adding to the complexity of patients' daily regimens. The selection of effective and well-tolerated treatment is a key step in the design of a combination tablet. Moreover, it is essential that the components have complementary mechanisms of action and compatible pharmacokinetic profiles.

Metformin represents the only oral antidiabetic agent proven to reduce the total burden of microvascular and macrovascular diabetic complications and to prolong the lives of Type 2 diabetic patients. Furthermore, metformin treatment is often associated with reductions in body weight in overweight patients and with improvements in lipid profiles in dyslipidemic patients. Metformin hydrochloride is marketed in the U.S. and elsewhere as either immediate-release or extended-release formulations with tablet dosage strengths of 500, 750, 850, and 1000 milligrams.

Dipeptidyl peptidase-IV (DPP-4) inhibitors represent a class of agents developed for the treatment or improvement in glycemic control in patients with Type 2 diabetes. For example, oral administration of the specific DPP-4 inhibitors sitagliptin, vildagliptin, alogliptin, and saxagliptin to human Type 2 diabetics has been found to reduce fasting glucose and postprandial glucose excursion in association with significantly reduced $HbA_{1c}$ levels. For reviews on the application of DPP-4 inhibitors for the treatment of Type 2 diabetes, reference is made to the following publications: (1) A. H. Stonehouse, et al., "Management of Type 2 diabetes: the role of incretin mimetics, *Exp. Opin. Pharmacother.*, 7: 2095-2105 (2006); (2) B. D. Green, et al., "Inhibition of dipeptidyl peptidase-IV activity as a therapy of Type 2 diabetes," *Exp. Opin. Emerging Drugs*, 11: 525-539 (2006); (3) M. M. J. Combettes, "GLP-1 and Type 2 diabetes: physiology and new clinical advances," *Curr. Opin. Pharmacol.*, 6: 598-605 (2006); and R. K. Campbell, "Rationale for Dipeptidyl Peptidase 4 Inhibitors: A New Class of Oral Agents for the Treatment of Type 2 Diabetes Mellitus," *Ann. Pharmacother.*, 41: 51-60 (2007).

Sitagliptin phosphate having structural formula I below is the dihydrogenphosphate salt of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine.

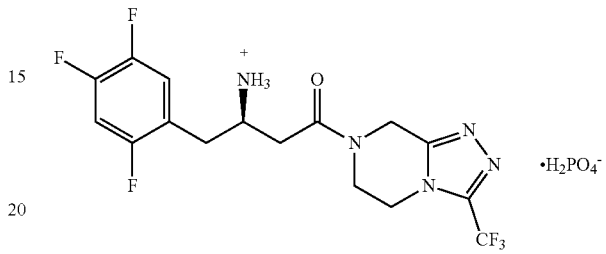

(I)

Sitagliptin phosphate can be in the form of a crystalline monohydrate. Sitagliptin free base and pharmaceutically acceptable salts thereof are disclosed in U.S. Pat. No. 6,699,871, the contents of which are hereby incorporated by reference in their entirety. Crystalline sitagliptin phosphate monohydrate is disclosed in U.S. Pat. No. 7,326,708, the contents of which are hereby incorporated by reference in their entirety. Sitagliptin phosphate has been approved for marketing in several countries, including the U.S., Europe, Canada, and Mexico, for the treatment of Type 2 diabetes and is branded as JANUVIA™ in the U.S. and elsewhere. For reviews, see D. Drucker, et al., "Sitagliptin," *Nature Reviews Drug Discovery*, 6: 109-110 (2007); C. F. Deacon, "Dipeptidyl peptidase 4 inhibition with sitagliptin: a new therapy for Type 2 diabetes," *Exp. Opin. Invest. Drugs*, 16: 533-545 (2007); K. A. Lyseng-Williamson, "Sitagliptin," *Drugs*, 67: 587-597 (2007); and B. Gallwitz, "Sitagliptin: Profile of a Novel DPP-4 Inhibitor for the Treatment of Type 2 Diabetes (Update)," *Drugs of Today*, 43: 801-814 (2007).

Sitagliptin can also be provided as a sitagliptin tannate complex. International Pub. No. WO2015/160678 published Oct. 22, 2015 discloses a sitagliptin tannate complex or pharmaceutical compositions or pharmaceutically acceptable intermediates comprising such a complex. The publication indicates that the complex possesses a release property or profile in which the complex exhibits a negligible release rate at neutral pH, and an immediate release in acidic pH. According to the publication, this release property allows formulation of sitagliptin in oral dosage form that is easier to swallow and does not need a film layer because the sitagliptin tannate complex has a neutral taste in the mouth.

The combination of sitagliptin and metformin provides substantial and additive glycemic improvement in patients with Type 2 diabetes (B. J. Goldstein, et al., "Effect of Initial Combination Therapy with Sitagliptin, a DPP-4 Inhibitor, and Metformin on Glycemic Control in Patients with Type 2 Diabetes," *Diabetes Care*, 30: 1979-1987 (2007) and B. Gallwitz, "Sitagliptin with Metformin: Profile of a combination for the treatment of Type 2 diabetes," *Drugs of Today*, 43: 681-689 (2007). A fixed-dose combination of immediate-release of both metformin and sitagliptin has been approved for marketing in several countries, including U.S. and Mexico, for adult patients with Type 2 diabetes who are not adequately controlled on metformin or sitagliptin alone or in patients already being treated with the combination of sitagliptin and metformin. The combination is branded as JANUMET™ in the U.S. JANUMET™ tablets contain 50 mg sitagliptin and either 500, 850, or 1000 mg metformin. Pharmaceutical compositions comprising fixed-dose combinations of immediate-release sitagliptin and immediate-release metformin are disclosed in U.S. Pat. No. 8,414,921.

U.S. Pat. Appl. Pub. No. 2010/0323011 also discloses pharmaceutical compositions comprising fixed-dose combinations of metformin, or a pharmaceutically acceptable salt thereof, coated with a form of the DPP-4 inhibitor sitagliptin or a pharmaceutically acceptable salt thereof. The publication discloses that the pharmaceutical compositions comprise an extended-release form of metformin, or a pharmaceutically acceptable salt thereof, and an immediate-release form of sitagliptin, or a pharmaceutically acceptable salt thereof.

While oral dosage forms that combine fixed doses of both sitagliptin and metformin represent an improved therapy over separate administration of the two active ingredients, further improvements to the dosage forms can result in further benefits to the patient population. For instance, oral dosage forms that are chewable may improve the combination therapy's appeal for patients, such as the elderly, who have difficulty swallowing a more rigid tablet or a capsule formulation of the combined active ingredients.

SUMMARY OF THE INVENTION

In one aspect, the present invention provides a chewable dosage form having a matrix comprising: a combination of active pharmaceutical ingredients which is metformin hydrochloride and sitagliptin or a pharmaceutically acceptable salt thereof;
    a fully or partially pregelatinized starch,
    a polyethylene glycol polymer;
    a lubricant;
    an emulsifier;
    a flavoring agent;
    and a sweetener.

In another aspect, the present invention provides a method of treating diabetes, e.g., non-insulin dependent (Type 2) diabetes mellitus, comprising administering a therapeutically effective amount of the chewable dosage form to a mammalian patient in need thereof.

DETAILED DESCRIPTION OF THE INVENTION

Figure 1:
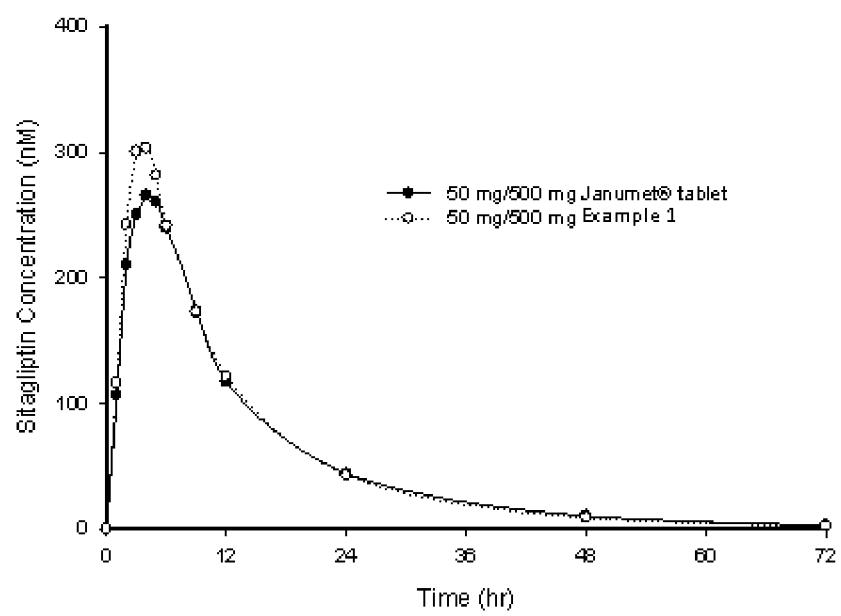
FIG. 1 shows the arithmetic mean plasma levels of sitagliptin (nM) following a single oral administration of a chewable dosage form of 50 mg sitagliptin/500 mg metformin as compared to a 50 mg sitagliptin/500 mg metformin (Janumet™) which is a marketed fixed-dose combination tablet of immediate-release metformin hydrochloride and immediate-release sitagliptin phosphate.

One aspect of the present invention is directed to pharmaceutical compositions which are chewable dosage form.

In embodiment no. 1, the present invention provides a chewable dosage form having a matrix comprising:
    a combination of active pharmaceutical ingredients which is metformin hydrochloride and sitagliptin or a pharmaceutically acceptable salt thereof;
    a fully or partially pregelatinized starch,
    a polyethylene glycol polymer;
    a lubricant;
    an emulsifier;
    a flavoring agent; and
    a sweetener.

In embodiment no. 2, the present invention provides the chewable dosage form as set forth in embodiment no. 1, wherein the sum of the fully or partially pregelatinized starch, lubricant, and polyethylene glycol polymer is at least 20 wt. % of the matrix. In embodiment no. 3, the sum of the fully or partially pregelatinized starch, lubricant, and polyethylene glycol polymer is 25-50 wt. % of the matrix.

In embodiment no. 4, the present invention provides the chewable dosage form as set forth in any one of embodiment nos. 1-3, wherein the emulsifier is glycerol monostearate or cetyl alcohol.

In embodiment no. 5, the present invention provides the chewable dosage form of any one of embodiment nos. 1-4, wherein the matrix further comprises an acidifier selected from organic acids such as citric acid, malic acid, acetic acid, lactic acid and tartaric acid. Preferably the acidifier is citric acid or malic acid.

In embodiment no. 6, the present invention provides the chewable dosage form of any one of embodiment nos. 1-5, wherein the matrix further comprises a humectant, wherein the humectant is glycerin, propylene glycol, or cetyl alcohol.

In embodiment no. 7, the present invention provides the chewable dosage form of any one of embodiment nos. 1-6, wherein the fully or partially pregelatinized starch is partially pregelatinized starch. In embodiment no. 8, the pregelatinized starch is STARCH 1500.

In embodiment no. 9, the present invention provides the chewable dosage form of any one of embodiment nos. 1-8, wherein the polyethylene glycol polymer is polyethylene glycol 8000, polyethylene glycol 6000 or polyethylene glycol 3350.

In embodiment no. 10, the present invention provides the chewable dosage form of any one of embodiment nos. 1-9, wherein the sweetener is a hydrogenated starch hydrolysate, a sugar alcohol, sucralose, glycyrrhizin or a pharmaceutically acceptable salt thereof, or a combination thereof.

In embodiment no. 11, the present invention provides the chewable dosage form of any one of embodiment nos. 1-10, wherein the lubricant is a vegetable oil lubricant, which is partially hydrogenated palm kernel oil, soy bean oil, or coconut oil.

In embodiment no. 12, the present invention provides the chewable dosage form of any one of embodiment nos. 1-11, wherein the flavoring agent is peppermint.

In embodiment 13, the present invention provides the chewable dosage form as set forth in embodiment no. 1, wherein the matrix comprises:
    from 15 to 40 wt. % of the combination of active pharmaceutical ingredients;
    from 25 to 45 wt. % of the fully or partially pregelatinized starch;
    from 0.5 to 10 wt. % of the polyethylene glycol polymer; and
    from 5 to 20 wt. % of the lubricant.

In embodiment 14, the present invention provides the chewable dosage form as set forth in embodiment no. 13, wherein the matrix comprises:

from 15 to 40 wt. % of the combination of active pharmaceutical ingredients;
from 25 to 45 wt. % of the fully or partially pregelatinized starch;
from 0.5 to 10 wt. % of polyethylene glycol 8000; and
from 5 to 20 wt. % of partially hydrogenated palm kernel oil.

The unit dosage strengths of sitagliptin free base anhydrate (active pharmaceutical ingredient) for inclusion into the soft chewable dosage forms as set forth in any one of embodiment nos. 1-14 are 25, 50 and 100 milligrams. Equivalent amounts of sitagliptin phosphate monohydrate to the stagliptin free base anhydrate are used in the pharmaceutical compositions, namely 32.125, 64.25, and 128.5 milligrams, respectively.

The unit dosage strengths of metformin hydrochloride (active pharmaceutical ingredient) for inclusion into the soft chewable dosage forms as set forth in any one of embodiment nos. 1-14 are 250, 500, 750, 850 and 1000 milligrams. These unit dosage strengths of metformin hydrochloride represent the the dosage strengths approved in the United States for marketing to treat Type 2 diabetes.

Specific embodiments of dosage strengths for sitagliptin and metformin hydrochloride in any one of the chewable dosage forms as set forth in embodiment no. 1-4 are the following:

(1) 25 milligrams of sitagliptin (equivalent to 32.125 milligrams of sitagliptin phosphate monohydrate) and 250 milligrams metformin hydrochloride;
(2) 25 milligrams of sitagliptin (equivalent to 32.125 milligrams of sitagliptin phosphate monohydrate) and 500 milligrams metformin hydrochloride;
(3) 25 milligrams of sitagliptin (equivalent to 32.125 milligrams of sitagliptin phosphate monohydrate) and 750 milligrams metformin hydrochloride;
(4) 25 milligrams of sitagliptin (equivalent to 32.125 milligrams of sitagliptin phosphate monohydrate) and 850 milligrams metformin hydrochloride;
(5) 25 milligrams of sitagliptin (equivalent to 32.125 milligrams of sitagliptin phosphate monohydrate) and 1000 milligrams metformin hydrochloride;
(6) 50 milligrams of sitagliptin (equivalent to 64.25 milligrams of sitagliptin phosphate monohydrate) and 500 milligrams metformin hydrochloride;
(7) 50 milligrams of sitagliptin (equivalent to 64.25 milligrams of sitagliptin phosphate monohydrate) and 750 milligrams metformin hydrochloride;
(8) 50 milligrams of sitagliptin (equivalent to 64.25 milligrams of sitagliptin phosphate monohydrate) and 850 milligrams metformin hydrochloride;
(9) 50 milligrams of sitagliptin (equivalent to 64.25 milligrams of sitagliptin phosphate monohydrate) and 1000 milligrams metformin hydrochloride;
(10) 100 milligrams of sitagliptin (equivalent to 128.5 milligrams of sitagliptin phosphate monohydrate) and 500 milligrams metformin hydrochloride;
(11) 100 milligrams of sitagliptin (equivalent to 128.5 milligrams of sitagliptin phosphate monohydrate) and 750 milligrams metformin hydrochloride;
(12) 100 milligrams of sitagliptin (equivalent to 128.5 milligrams of sitagliptin phosphate monohydrate) and 850 milligrams metformin hydrochloride; and
(13) 100 milligrams of sitagliptin (equivalent to 128.5 milligrams of sitagliptin phosphate monohydrate) and 1000 milligrams metformin hydrochloride.

A preferred pharmaceutically acceptable salt of sitagliptin for any of the above-described embodiments is the dihydrogenphosphate salt of structural formula I above (sitagliptin phosphate). A preferred form of the dihydrogenphosphate salt is the crystalline monohydrate disclosed in U.S. Pat. No. 7,326,708, the contents of which are hereby incorporated by reference in their entirety.

Another preferred form of sitagliptin for any of the above-described embodiments is a sitagliptin tannate complex. A preferred form of this sitagliptin complex is the one prepared and disclosed in Example 1 of US Patent Application Publication No. 20170042922. Briefly, the sitagliptin tannate complex can be prepared by combining a salt or a free base form of sitagliptin in a suitable solvent with a dispersion of tannic acid in a suitable solvent, removing the liquid; washing the residue with a polar pharmaceutically acceptable liquid; drying the residue; and pulverizing the sitagliptin tannate complex into a free-flowing powder.

The preparation of sitagliptin and pharmaceutically acceptable salts thereof, are disclosed in U.S. Pat. No. 6,699,871.

Another aspect of the present invention is directed to a method of treating diabetes, e.g., non-insulin dependent (Type 2) diabetes mellitus, comprising administering a therapeutically effective amount of the chewable dosage form as described in any of the embodiments described above to a mammalian patient in need thereof. In preferred embodiments, the mammalian patient being treated is a human patient.

The terms "therapeutically effective amount" and similar descriptions such as "an amount efficacious for treatment" are intended to mean that amount of a pharmaceutical drug or combination of drugs that will elicit the biological or medical response of a tissue, a system, animal or human that is being sought by a researcher, veterinarian, medical doctor or other clinician. In a preferred embodiment, the term "therapeutically effective amount" means an amount of a pharmaceutical drug that alleviates at least one clinical symptom in a human patient. The terms "prophylactically effective (or efficacious) amount" and similar descriptions such as "an amount efficacious for prevention" are intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The dosage regimen utilizing a dosage form of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of Type II diabetes, and a prophylactically effective amount, e.g., for prevention of Type II diabetes.

The soft chewable dosage form contains food grade and compendial excipients only, and preferably are not of animal origin. The excipients for the soft chewable dosage forms can include, but are not limited to the following excipients: favorants, sweeteners, emulsifiers, binders, gums, fillers, texture, modifiers, absorbents, lubricants, mouth-feel enhancers, acidifiers, humectants, anti-sticking agents, anti-caking agents, wetting agents, colorants, and other excipients familiar to those skilled in the art. Optionally, in addition to sweeteners incorporated into the matrix to make the dosage forms palatable and appealing, other taste masking approaches may be used, such as encapsulation or complexation of the active ingredients.

The chewable dosage forms of the invention include a fully or partially pregelatinized starch which serve as a filler and impart the chewy texture of the soft chew dosage forms of the present invention. "Pregelatinized starch" as meant herein, and as disclosed in USP26/N21 refers to starch that has been chemically and/or mechanically processed to rupture all or part of the granules in the presence of water and is subsequently dried. "Fully or partially pregelatinzed starch" as used herein, refers to a starch wherein at least some fraction of the starch is gelatinized, up to, and including the entire quantity of starch. As will be recognized by formulators of skill in the art, fully pregelatinized starch is readily soluble in water. Such starches also can function as binders and texture enhancers. Other bulking agents or fillers can also be included in the dosage forms of the invention along with the fully or partially pregelatinized starch. Such other bulking agents or fillers include polysaccharides, pharmaceutical gums, and polymers. Pharmaceutical gums such as xanthan gum, pectins, carboxymethyl cellulose, gelatin, and others known to those skilled in the art can impart the chewy texture of the soft chew dosage forms of the present invention.

Waxes are added to the formulation so that the soft chew dosage forms do not stick together upon molding. Waxes, such as polyethylene glycol, are added into the formulations, preferably as a melt. The waxes also aid in maintaining the shape or form of the dosage form. Preferred waxes include polyethylene glycol 8000, polyethylene glycol 6000, or polyethylene glycol 3350. Typically, the wax is present in the dosage forms from 0.1-10 wt. %, and preferably from 1-5 wt. %.

In certain embodiments, lubricants, anti-sticking agents, and anti-caking agents are included in the soft chewable dosage forms of the invention into the formulation to facilitate the manufacturing process. Inclusion of a vegetable oil such as partially hydrogenated palm kernel oil, soy bean oil, or coconut oil suitably serves this purpose.

Since the formulation contains both oils and excipients that are water-soluble, to facilitate the formation of a homogeneous mixture, incorporation of one or more emulsifiers is advantageous. A preferred emulsifier is glycerol monostearate, though others can be included, such as cetyl alcohol, which can also serve as as a wetting agent. Other wetting agents such as sodium lauryl sulfate and polyethylene glycols can be included along with the emulsifier.

The chewable dosage forms of the present invention include flavoring agents. Suitable flavoring agents include peppermint, cherry, banana, mango, orange, pineapple, raspberry, strawberry, or vanilla.

The soft chewable dosage forms of the invention typically include hydrogenated starch hydrolysates, such as Lycasin® 85/55, as a bulk sweetener. Sugar alcohols can also serve as a sucrose substitute, and optionally, can be used with high intensity artificial sweeteners, such as sucralose and glycyrrhizin.

In some embodiments, the soft chewable dosage forms of the invention include humectants to maintain the forms' soft texture. A preferred humectant is glycerin, but other humectants such as propylene glycol and cetyl alcohol can serve as humectants.

In certain embodiments, the soft chewable forms of the invention include an acidifier such as citric acid, malic acid, acetic acid, lactic acid or tartaric acid.

In certain embodiments, a super-disintegrant, preferably sodium starch glycolate or similar disintegrant such as starch USP, starch 800, alginic acid, sodium croscarmellose, crospovidone, or polyplasdone can be added to aid in the disintegration of the soft chew dosage forms if swallowed wholly or in large pieces.

Some embodiments of the soft chew dosage forms of the invention include a preservative or a combination of preservatives into the formulation to prevent microbial contamination over the shelf life of the dosage form. Examples of such preservatives include, but are not limited to, sodium sorbate, methyl paraben, and others well-known to those skilled in the art.

The individual amount of each excipient in the soft chew dosage forms of the invention can vary considerably depending on factors, such as the drug load, desired texture, image size and other factors known to those skilled in the art.

General Method for Preparing the Soft Chewable Dosage Forms

The soft chewable dosage forms of the present invention can be prepared by following the general process described below. The description of the process provided to more clearly describe the present invention and should not be construed to limit the scope of the invention.

a. Mix, under the appropriate shear, hydrogenated starch hydrolysate (a sweetener), optional humectant, optional acidifier, flavoring agent, optional colorant, optional pharmaceutical gum and a sweetener;

b. Blend the ingredients from step (a) with the lubricant (e.g., vegetable oil), and an emulsifier (if using fat or a solid emulsifier, such as glycerol monostearate, use a melt of the same);

c. Add and blend a wax (anti-sticking agent), such as polyethylene glycol, to the mixture of step (b);

d. Mix under high shear the blend of active pharmaceutical ingredients (or taste-masekd active pharmaceutical ingredients) and a filler, such as STARCH 1500 (a mixture of fully and partially pregelatinized starch), with the mixture of step (c);

e. Remove the resultant dough-like mixture from the mixer; and f. Mold the matrix from step (e) into individual unit masses with the uniform content of active pharmaceutical ingredients.

EXAMPLES

The following examples are provided to more clearly describe the present invention and should not be construed to limit the scope of the invention.

Example 1

Preparation and of a Sitagliptin/Metformin HCl Soft Chew Dosage Form Equipment and Supplies

| Ingredient | Grade | Function | Manufacturer | Quantity (mg/chew) | Quantity (g/batch) |
|---|---|---|---|---|---|
| Metformin HCl | USP | Active | Farmhispania | 500.0 | 20.0 |
| Sitagliptin phosphate monohydrate | N/A | Active | Merck | 64.3 | 2.6 |
| Partially pregelatinized Starch [Starch 1500] | USP/NF | Filler | Colorcon | 808.2 | 32.3 |
| Maltitol syrup [Lycasin 85/55] | USP/NF | Sweetener | Roquette America, Inc. | 575.0 | 23.0 |
| Partially hydrogenated palm kernel oil | NF | Lubricant/mouth-feel enhancer | IOI Loders Croklaan | 300.0 | 12.0 |
| Glycerin | USP/NF | Humectant | Procter & Gamble | 125.0 | 5.0 |
| PEG 8000 | USP/NF | Binder | Dow Chemical | 75.0 | 3.0 |
| Citric acid, anhydrous | USP/NF | Acidifier/Flavor | Archer Daniels Midland | 12.5 | 0.5 |
| Peppermint | Food | Flavor | Virginia Dare | 12.5 | 0.5 |
| Sucralose powder | NF | Sweetener | Tate & Lyle | 12.5 | 0.5 |
| Glyceryl monostearate [IMWITOR 491] | USP/NF | Emulsifier | Cremer Leo Division | 12.5 | 0.5 |
| Ammonium glycyrrhizate [magnasweet 100] | EP | Sweetener | Mafco | 2.5 | 0.1 |
| Total | | | | 2500.0 | 100.0 |

N/A stands for 'not applicable'

Preparation

All weights were determined on an analytical balance.

1. 2600 mg (±78 mg) of sitagliptin phosphate monohydrate was weighed into a glass mortar.

2. Ingredients 2.a-2.e were added, respectively, to the mortar in Step 1, mixing for at least 60 seconds after each addition (geometric dissolution) using a stainless steel spatula until the powder blend appeared to be uniformly mixed.
   a. 2600 mg (±78 mg) STARCH 1500;
   b. 5200 mg (±156 mg) STARCH 1500;
   c. 10000 mg (±300 mg) STARCH 1500;
   d. 20000 mg (±600 mg) metformin hydrochloride;
   e. 14500 mg (±400 mg) starch 1500.

3. 23000 mg (±700 mg) of maltitol syrup was weighed into a 400 mL beaker and 5000 mg (±200 mg) of glycerin was added to the vessel.

4. 500 mg (±1 mg) of citric acid, 100 mg (±3 mg) of MAGNASWEET, 500 mg (±15 mg) of sucralose, and 500 mg (±15 mg) of peppermint were added to the contents of the vessel described in step 3.

5. 300 mg (±90 mg) of PEG 8000 was weighed into a weighing boat.

6. 12000 mg (±400 mg) of partially hydrogenated palm kernel oil and 500 mg (±15 mg) of glyceryl monostearate were added into a 25 mL beaker. The contents were melted together at 70-80° C. on a hotplate. The resulting melt and the PEG 8000 from step 5 were added to the contents in the vessel of step 4.

7. The powder blend from step 1 was added to the viscous mixture formed in step 6. The mixture was mixed using a stainless steel spatula for at least 3 minutes until a uniform dough-like matrix formed.

8. 2500 mg (±75 mg) of the matrix formed in step 7 was formed into a ball to form the soft chew dosage form.

9. Step 8 was repeated until 40 soft chew dosage forms were prepared.

10. The soft chew dosage forms from steps 8 and 9 were allowed to set for 2 hours.

11. The soft chew dosage forms were individually wrapped with wax paper. The wrapped, dosage forms were stored in a 250 mL amber glass bottle fitted with a screw cap at 20±5° C.

Example 2

Pharmacokinetic Analysis of Patients Following Administration of Soft Chew Dosage Forms A study was conducted to estimate the pharmacokinetic (PK) parameters ($AUC_{0-\infty}$, $AUC_{0-last}$, $C_{max}$, $T_{max}$ and apparent terminal $t_{1/2}$) following a single dose administration of the sitagliptin/metformin 50 mg/500 mg soft chew dosage forms of Example 1. The study was an open-label, 3-period, fixed sequence study. Sixteen healthy, non-tobacco using male and female subjects were enrolled to complete the study with at least 12 subjects. In each period, subjects received a single soft chew dosage form of Example 1 administered as one of three treatments under fed conditions. Treatment A consisted of administration of the reference Janumet™ 50 mg/500 mg oral tablet. Treatment B consisted of administration of the 50 mg/500 mg soft chew dosage forms of Example 1.

Blood sampling for PK evaluation was performed for sitagliptin and metformin at predose (0), 1, 2, 3, 4, 5, 6, 9, 12, 24, 48 and 72 hours for each period.

As shown in FIG. 1, for the observed sitagliptin plasma concentration, the $C_{max}$, $AUC_{0-last}$ and $AUC_{0-\infty}$ arithmetic values were less than 4% higher following the administration of the dosage forms of Example 1 when compared with the arithmetic values resulting from the administration of the 50 mg/500 mg Janumet™ mg oral tablet.

Figure 2:
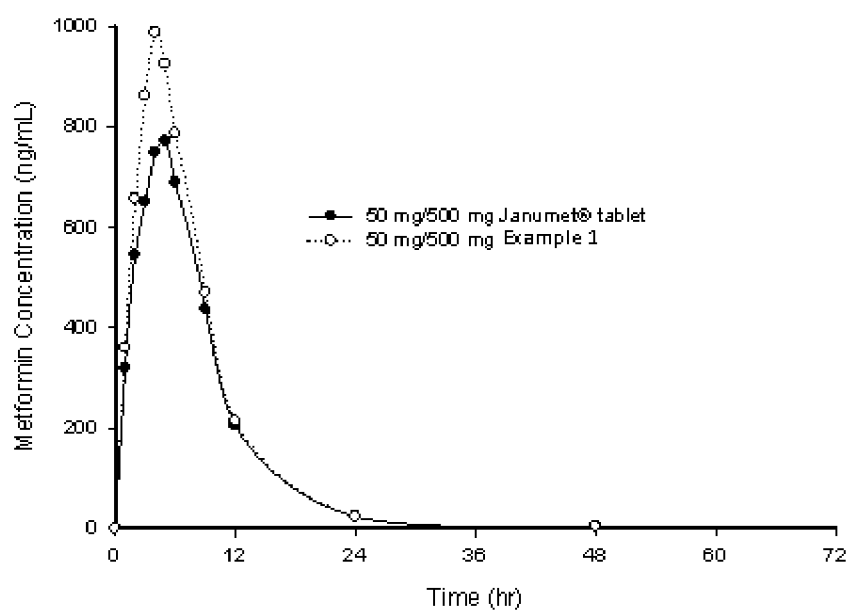
FIG. 2 shows the arithmetic mean plasma levels of metformin (nM) following a single oral administration of a chewable dosage form of 50 mg sitagliptin/500 mg metformin as compared to a 50 mg sitagliptin/500 mg metformin (Janumet™) which is a marketed fixed-dose combination tablet of immediate-release metformin hydrochloride and immediate-release sitagliptin phosphate.

As shown in FIG. 2, for the observed metformin plasma concentration, the $C_{max}$, $AUC_{0-last}$ and $AUC_{0-\infty}$ arithmetic values were approximately 15-24% higher following the administration of the dosage forms of Example 1 when compared with the GM values resulting from the administration of the 50 mg/500 mg Janumet™ oral tablet.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A chewable dosage form having a matrix comprising:
   from 15 to 40 wt. % of a combination of active pharmaceutical ingredients which is metformin hydrochloride and sitagliptin or a pharmaceutically acceptable salt thereof;
   from 25 to 45 wt. % of a fully or partially pregelatinized starch;
   from 0.5 to 10 wt. % of a polyethylene glycol 8000;
   from 5 to 20 wt. % of a lubricant, wherein the lubricant is partially hydrogenated palm kernel oil;
   an emulsifier;
   a flavoring agent; and
   a sweetener;
   and
   wherein the dosage form is chewable.

2. The chewable dosage form of claim 1, wherein the emulsifier is glycerol monostearate or cetyl alcohol.

3. The chewable dosage form of claim 1, wherein the matrix further comprises an acidifier wherein the acidifier is citric acid, malic acid, acetic acid, lactic acid or tartaric acid.

4. The chewable dosage form of claim 1, wherein the matrix further comprises a humectant, wherein the humectant is glycerin, propylene glycol, or cetyl alcohol.

5. The chewable dosage form of claim 1, wherein the sweetener is a hydrogenated starch hydrolysate, a sugar alcohol, sucralose, glycyrrhizin or a pharmaceutically acceptable salt thereof, or a combination thereof.

6. The chewable dosage form of claim 1, wherein the flavoring agent is peppermint.

7. The chewable dosage form of claim 1, wherein the combination of active pharmaceutical ingredients is 500 mg of metformin hydrochloride and 50 mg of sitagliptin.

8. A method for treating diabetes, comprising administering a therapeutically effective amount of the chewable dosage form of claim 1 to a mammalian patient in need thereof.

9. A method for treating non-insulin dependent diabetes mellitus, comprising administering a therapeutically effective amount of the chewable dosage form of claim 1 to a mammalian patient in need thereof.

* * * * *